United States Patent [19]

Kormány et al.

[11] 4,066,830
[45] Jan. 3, 1978

[54] BENZOXAZOLE-STYRYLS

[75] Inventors: Géza Kormány, Allschwil; Guglielmo Kabas, Aesch, both of Switzerland

[73] Assignee: Ciba-Geigy Corporation, Ardsley, N.Y.

[21] Appl. No.: 663,189

[22] Filed: Mar. 3, 1976

[30] Foreign Application Priority Data

Mar. 11, 1975 Switzerland .......................... 3059/75

[51] Int. Cl.² .......................................... C07D 413/10
[52] U.S. Cl. ..................... 542/456; 8/1 W; 252/301.24; 427/158; 542/435
[58] Field of Search ............ 260/240 D, 240.1, 240 C, 260/249 CA

[56] References Cited

U.S. PATENT DOCUMENTS

| | | |
|---|---|---|
| 3,635,959 | 1/1972 | di Giovanoel et al. .......... 260/240 D |
| 3,732,213 | 5/1973 | Balzer et al. ................. 260/240 CA |
| 3,891,632 | 6/1975 | Fleck et al. ...................... 260/240 D |
| 3,926,969 | 12/1975 | Fleck et al. ...................... 260/240 D |

FOREIGN PATENT DOCUMENTS 2,025,792  12/1970  Germany.
2,262,340  6/1973  Germany.

OTHER PUBLICATIONS

Neuner et al., Chemical Abstracts, 75 (1971), #152985m.

Primary Examiner—Arthur P. Demers
Attorney, Agent, or Firm—Edward McC. Roberts; Prabodh I. Almaula

[57] ABSTRACT

The invention is directed to new benzoxazole-styryls of the formula

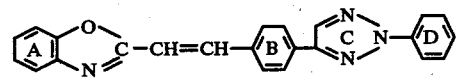

wherein the rings A, B, C and D can be substituted, as well as processes for their preparation. The invention relates also to a process for optically brightening high-molecular organic materials on using said compounds.

7 Claims, No Drawings

BENZOXAZOLE-STYRYLS

The present invention relates to new benzoxazole-styryls, processes for their manufacture and their use for the optical brightening of high-molecular organic materials.

The new benzoxazole-styryls correspond to the formula

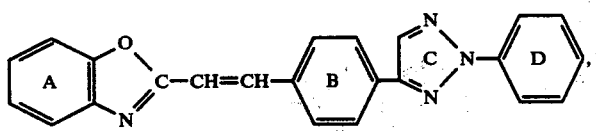

(1)

wherein the rings A, B, C and D can carry non-chromophoric substituents.

Within the scope of the formula (1), compounds which are of interest are, above all, those of the formula

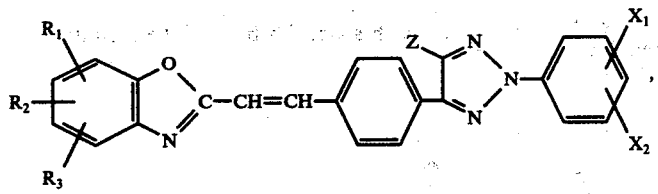

(2)

wherein $R_1$ denotes hydrogen, unsubstituted alkyl with 1 to 4 carbon atoms, alkyl, with 1 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylalkyl with 1 to 3 carbon atoms in the alkyl part, phenyl which is optionally substituted by 1 or 2 substituents from the series chlorine, methyl or methoxy; alkoxy with 1 to 4 carbon atoms, phenoxy which is optionally substituted by 1 or 2 substituents from the series chlorine, methyl or methoxy; chlorine, bromine, cyano, COOR, wherein R represents hydrogen, a salt-forming cation, alkyl with 1 to 5 carbon atoms or benzyl, CONR' ($R_1'$), wherein R' represents hydrogen, alkyl with 1 to 6 carbon atoms, alkyl, with 2 to 4 carbon atoms, which is substituted at the terminal carbon atom by a dialkylamino group or an optionally quaternised dialkylamino group with 1 to 4 carbon atoms in each alkyl part, hydroxyalkyl with 1 to 4 carbon atoms, alkoxyalkyl with 2 to 8 carbon atoms, phenyl or benzyl and $R_1'$ represents hydrogen, alkyl with 1 to 6 carbon atoms, hydroxyalkyl with 1 to 4 carbon atoms or alkoxyalkyl with 2 to 8 carbon atoms, or R' and $R_1'$, conjointly with the nitrogen, represent a morpholino or piperidino radical; $SO_2OY$, wherein Y denotes hydrogen, a salt-forming cation, alkyl with 1 to 5 carbon atoms, phenyl or alkyl-substituted phenyl, $SO_2NR'$ ($R_1'$), wherein R' and $R_1'$ have the meaning indicated above, alkylsulphonyl with 1 to 6 carbon atoms, benzylsulphonyl, phenylsulphonyl or phenylsulphonyl which is substituted by chlorine or methyl, or $R_1$, conjointly with $R_2$, denotes a fused phenyl ring, $R_2$ denotes hydrogen, alkyl with 1 to 5 carbon atoms, alkoxy with 1 to 4 carbon atoms or chlorine or, conjointly with $R_1$, a fused phenyl ring, $R_3$ denotes hydrogen or methyl, $X_1$ denotes hydrogen, alkyl with 1 to 4 carbon atoms, cyclohexyl, phenylalkyl with 1 to carbon atoms in the alkyl part, phenyl, alkoxy with 1 to 4 carbon atoms, phenoxy, chlorine, cyano, COOR, CONR' ($R_1'$), $SO_2OY$, $SO_2NR'$ ($R_1'$), wherein Y, R, R' and $R_1'$ each have the abovementioned meaning, alkylsulphonyl with 1 to 6 carbon atoms, benzylsulphonyl, phenylsulphonyl or phenylsulphonyl which is optionally substituted by chlorine or methyl, $X_2$ denotes hydrogen, chlorine, methyl or methoxy and Z denotes hydrogen, chlorine or phenyl.

Of particular practical interest are the benzoxazole-styryls of the formula

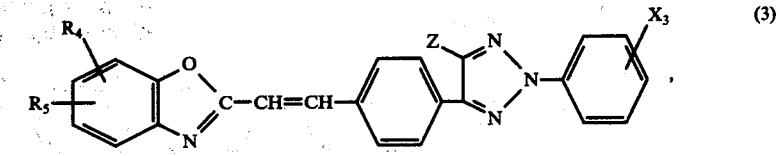

(3)

wherein $R_4$ denotes hydrogen, chlorine, unsubstituted alkyl with 1 to 4 carbon atoms, alkyl, with 2 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylalkyl with 1 to 3 carbon atoms in the alkyl part, phenyl or alkoxy with 1 to 4 carbon atoms, $R_5$ denotes hydrogen or alkyl with 1 to 4 carbon atoms, $X_3$ denotes hydrogen, alkyl with 1 to 4 carbon atoms, alkoxy with 1 to 4 carbon atoms, chlorine, carbalkoxy with 2 to 5 carbon atoms, sulphamoyl or sulphamoyl which is monosubstituted or disubstituted by alkyl with 1 to 4 carbon atoms or hydroxyalkyl with 2 to 4 carbon atoms, or alkylsulphonyl with 1 to 4 carbon atoms and Z denotes hydrogen, chlorine or phenyl.

Compounds to be singled out are those of the formula

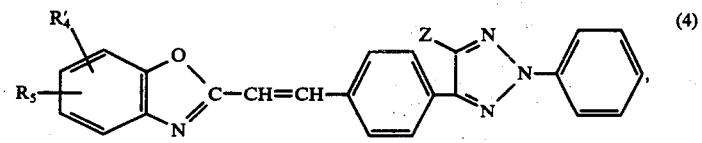

wherein R$_4'$ denotes hydrogen, chlorine, unsubstituted alkyl with 1 to 4 carbon atoms, alkyl, with 2 to 3 carbon atoms, which is substituted at the terminal carbon atom by a cyano group or COOR group, wherein R represents hydrogen, sodium, potassium or alkyl with 1 to 5 carbon atoms, cyclohexyl, phenyl, alkoxy with 1 to 4 carbon atoms or alkylsulphonyl with 1 to 4 carbon atoms, R$_5$ denotes hydrogen or alkyl with 1 to 4 carbon atoms and Z denotes hydrogen, chlorine or phenyl.

The compounds of the formula

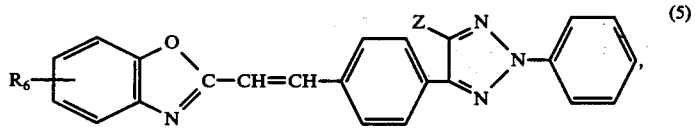

wherein R$_6$ denotes hydrogen, chlorine, alkyl with 1 to 4 carbon atoms, β-cyanoethyl, cyclohexyl, phenyl or alkoxy with 1 to 4 carbon atoms and Z denotes hydrogen, chlorine or phenyl, and of the formula

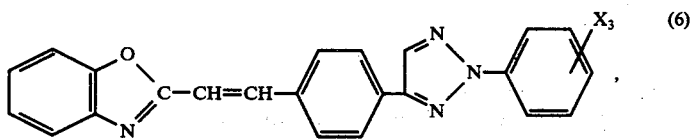

wherein X$_3$ denotes hydrogen, alkyl with 1 to 4 carbon atoms, alkoxy with 1 to 4 carbon atoms, chlorine, carbalkoxy with 2 to 5 carbon atoms, sulphamoyl which is optionally monosubstituted or disubstituted by alkyl with 1 to 4 carbon atoms or hydroxyalkyl with 2 to 4 carbon atoms, or alkylsulphonyl with 1 to 4 carbon atoms, also deserve particular mention.

The compound of the formula

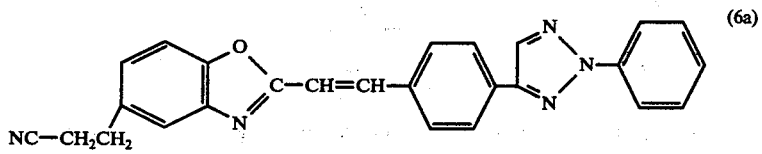

proves to be particularly valuable.

Possible salt-forming cations (symbols R and Y) are, inter alia, alkali metal ions or alkaline earth metal ions, ammonium ions which are optionally substituted by alkyl or hydroxyalkyl and amine salt ions of cyclic amines, such as, for example, pyridine, morpholine or piperidine. Sodium ions and potassium ions are preferred here.

R$_1$ in the formula (2), R$_4$ in the formulae (3) and (4) and R$_6$ in the formula (5) are preferably in the 5-position of the benzoxazole radical, whilst the p-position to the bond to the triazole radical is preferred for X$_1$ in the formula (2) or for X$_3$ in the formulae (3) and (6). Z preferably denotes hydrogen in the preceding formulae.

The new benzoxazole-styryls of the formula (1) can be manufactured according to various processes.

A large proportion of the new compounds can be manufactured according to a new process which is characterised in that a methyl compound of the formula

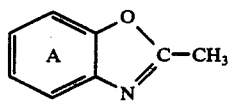

is reacted with a Schiff's base of the formula

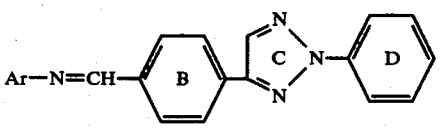

wherein Ar denotes an aromatic radical, in dimethylformamide as the reaction medium and in the presence of a strongly basic alkali metal compound, it being possible for the reaction mixture to be initially irradiated with ultraviolet light.

The irradiation with ultraviolet light is effected by a source applied either outside or inside the reaction vessel. The irradiation with ultraviolet light can be used for starting the reaction, and not for complete reaction of the reactants. Thus an irradiation time of a few minutes is mostly sufficient. Ultraviolet light with a wavelength of over 300 nm is preferably used.

The symbol Ar generally represents an optionally substituted naphthyl or, in particular, phenyl radical. Ar preferably represents the radical of the formula

 (9)

wherein h denotes hydrogen or chlorine.

In general, a compound of the formula $$MOC_{n-1}H_{2n-1} \quad (10)$$

wherein M denotes potassium or sodium and n denotes an integer from 1 to 6, is used as the strongly basic alkali metal compound.

Examples of compounds of the formula (10) which may be mentioned are sodium methylate, potassium tertiary-butylate, sodium hydroxide and potassium hydroxide.

In the case of alcoholates, the reaction should be carried out in a virtually anhydrous medium, whilst in the case of hydroxides contents of water of up to 25% are allowed.

In the case of potassium hydroxide, which is preferably to be used, a water content of up to about 15% has proved appropriate.

The compound containing the methyl group is appropriately reacted with the Schiff's base in equivalent amounts, so that no substantial excess of either component is present. At least the equivalent amount of the alkali metal compound is advantageously used, that is to say at least 1 mol of alkali metal compound per mol of Schiff's base. When potassium hydroxide is used preferably two times to eight times the equivalent amount is employed.

The reaction according to the invention can generally be carried out at temperatures in the range between about 10 and 40° C. If potassium hydroxide is used in the reaction the reaction generally already takes place at room temperature, in which case no external supply of heat is required.

If other alkali metal compounds are used, the reaction is to be carried out at elevated temperatures, depending on their basic strength. A reaction temperature as low as possible is, however, desirable, since side reactions, such as, for example, ring cleavage, can occur at higher temperatures.

The end products can be worked up from the reaction mixture according to customary methods which are in themselves known.

A large proportion of the compounds of the formula (1) and, for example, those of the formula

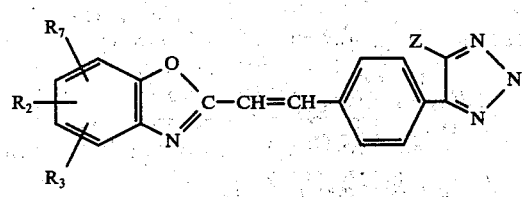 (11)

and

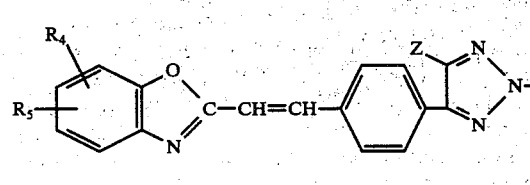 (12)

wherein $R_2$, $R_3$, $R_4$, $R_5$ and Z have the meaning indicated above and $R_7$ denotes hydrogen, unsubstituted alkyl with 1 to 4 carbon atoms, alkyl, with 1 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylalkyl with 1 to 3 carbon atoms in the alkyl part, phenyl which is optionally substituted by 1 or 2 substituents from the series chlorine, methyl or methoxy; alkoxy with 1 to 4 carbon atoms, phenoxy which is optionally substituted by 1 or 2 substituents from the series chlorine, methyl or methoxy; chlorine, bromine, cyano, COOR, wherein R represents hydrogen, a salt-forming cation, alkyl with 1 to 5 carbon atoms or benzyl, CONR' ($R_1'$), wherein R' represents hydrogen, alkyl with 1 to 6 carbon atoms, alkyl, with 2 to 4 carbon atoms, which is substituted at the terminal carbon atom by a dialkylamino group or an optionally quaternised dialkylamino group with 1 to 4 carbon atoms in each alkyl part, hydroxyalkyl with 1 to 4 carbon atoms, alkoxyalkyl with 2 to 8 carbon atoms, phenyl or benzyl and $R_1'$ represents hydrogen, alkyl with 1 to 6 carbon atoms, hydroxyalkyl with 1 to 4 carbon atoms or alkoxyalkyl with 2 to 8 carbon atoms, or R' and $R_1'$, conjointly with the nitrogen, represent a morpholino or piperidino radical, SO$_2$NR' ($R_1'$), wherein R' and $R_1'$ have the meaning indicated above, phenylsulphonyl or phenylsulphonyl which is substituted by chlorine, or $R_7$, conjointly with $R_2$, denotes a fused phenyl ring, $X_1'$ denotes hydrogen, alkyl with 1 to 4 carbon atoms, cyclohexyl, phenylalkyl with 1 to 3 carbon atoms in the alkyl part, phenyl, alkoxy with 1 to 4 carbon atoms, phenoxy, chlorine, unsubstituted phenylsulphonyl or phenylsulphonyl which is substituted by chlorine, $X_2'$ denotes hydrogen, chlorine, methyl or methoxy and $X_3'$ denotes hydrogen, alkyl with 1 to 4 carbon atoms, alkoxy with 1 to 4 carbon atoms, chlorine, carbalkoxy with 2 to 5 carbon atoms or sulphamoyl which is optionally monosubstituted or disubstituted by alkyl or hydroxyalkyl with 2 to 4 carbon atoms, are obtained in an analogous manner, by reacting a methyl compound of the formula

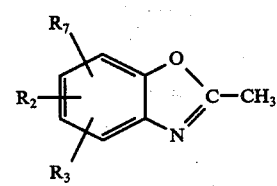 (13)

or

-continued

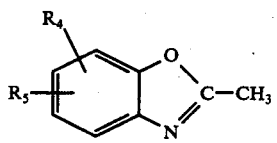

with a Schiff's base of the formula

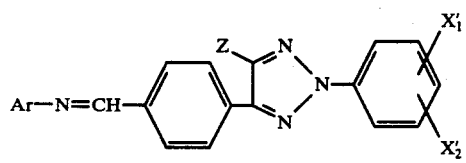

or

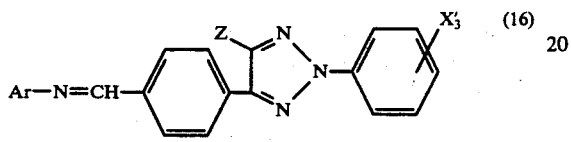

wherein $X_1'$, $X_2'$, $X_3'$, $R_2$, $R_3$, $R_4$, $R_5$, $R_7$, Z and Ar have the meaning indicated above.

The starting materials of the formulae (7), (8) and (13) to (16) are obtained analogously to processes which are in themselves known.

The compounds of the formulae (1) to (6a) can also be manufactured by reacting a methyl compound of the formulae (7), (13) or (14) with an aldehyde of the formula

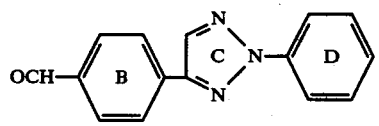

or

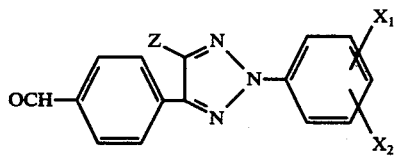

or

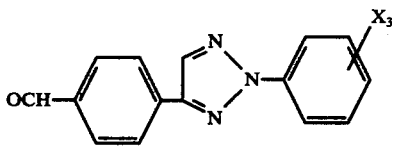

wherein the rings B, C and D and the substituents $X_1$, $X_2$, $X_3$ and Z have the meaning indicated above, in the presence of a catalyst which splits off water or in an inert, high-boiling solvent and in the presence of a catalyst, with the simultaneous removal of the water of reaction.

Possible catalysts which split off water are, for example, zinc chloride or acetic anhydride. Hydrocarbons and halogenated hydrocarbons such as, for example, xylene or chlorobenzene, can be used as inert, high-boiling solvents and, for example, p-toluenesulphonic acid together with dialkylformamide or dialkylacetamide, preferably dimethylformamide, can be used as catalysts for the condensation in the inert solvent.

Another process, which is in itself known, for the manufacture of most of the new compounds of the formula (1) consists in reacting a compound of the formula

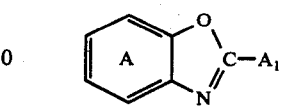

with a compound of the formula

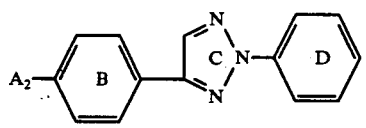

wherein the symbol $A_1$ denotes a grouping of the formula

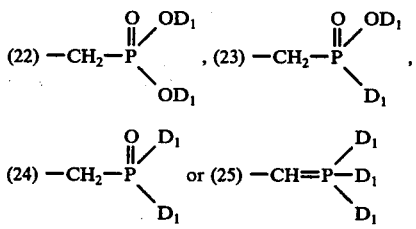

wherein $D_1$ represents an optionally further substituted alkyl radical, preferably an alkyl radical with up to 6 carbon atoms, an aryl radical, preferably a phenyl radical, a cycloalkyl radical, preferably a cyclohexyl radical, or an aralkyl radical, preferably a benzyl radical, and $A_2$ is a formyl group.

This manufacturing process is advantageously carried out in inert solvents. Examples of these which may be mentioned are hydrocarbons, such as toluene and xylene, or alcohols, such as methanol, ethanol, isopropanol, butanol, glycols, glycol ethers, such as 2-methoxyethanol, hexanols, cyclohexanol and cyclooctanol, and also ethers, such as diisopropyl ether, tetrahydrofurane and dioxane, as well as dimethylsulphoxide, formamide and N-methylpyrrolidone. Polar organic solvents, such as dimethylformamide and dimethylsulphoxide, are particularly suitable. Some of the reactions can also be carried out in aqueous solution.

The temperature at which the reaction is carried out can vary within wide limits. It is determined ($\alpha$) by the resistance of the solvent used to the strongly basic alkali metal compounds, ($\beta$) by the reactivity of the condensation partners and ($\gamma$) by the effectiveness of the solvent/base combination as a condensation agent.

In practice, accordingly, temperatures between 10° and 100° C are generally possible, in particular if dimethylformamide or dimethylsulphoxide is used as the solvent. The preferred temperature range is 20° to 60° C.

Possible strongly basic alkali metal compounds which can be used are, above all, the hydroxides, amides and alcoholates (preferably those of primary alcohols containing 1 to 4 carbon atoms) of the alkali metals, those of lithium, sodium and potassium being of predominant interest for economical reasons. However, in principle and in particular cases, alkali metal sulphides and carbonates, aryl-alkali metal compounds, such as, for example, phenyl-lithium, or strongly basic amines (including ammonium bases), for example trialkylammonium hydroxides, can also be used successfully.

The compounds of the formulae (2) to (6a) are manufactured in an equally corresponding manner, for example by reacting a compound of the formula

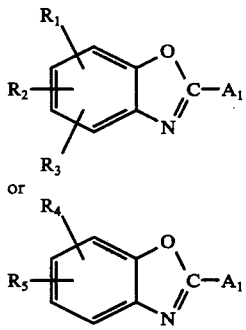

(26)

or (27)

with a compound of the formula

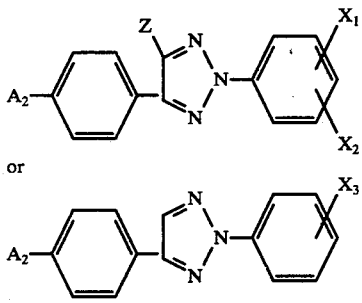

(28)

or (29)

wherein $R_1$ to $R_4$, $X_1$ to $X_3$, Z, $A_1$ and $A_2$ have the meanings indicated above.

The starting materials of the formulae (20) and (21) and (26) to (29) are known or are obtained analogously to processes which are in themselves known.

The new compounds defined above exhibit a more or less pronounced fluorescence in the dissolved or finely dispersed state. They can be used for optically brightening the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high-molecular materials a. Polymerisation products based on organic compounds containing at least one polymerisable carbon-carbon double bond, that is to say their homopolymers or copolymers as well as their after-treatment products such as, for example, cross-linking, grafting or degradation products, polymer blends or products obtained by modification of reactive groups, for example polymers based on α,β-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example polyamides of the polycaprolactam type, and also polymers which are obtainable both via polyaddition and via polycondensation, such as polyethers or polyacetals, c. Polycondensation products or precondensates based on bifunctional or polyfunctional compounds possessing condensable groups, their homocondensation and co-condensation products, and after-treatment products, such as, for example, polyesters, especially polyesters which are saturated (for example ethylene glycol terephthalic acid polyester) or unsaturated (for example maleic acid dialcohol polycondensates as well as their crosslinking products with copolymerisable vinyl monomers), unbranched or branched (also including those based on polyhydric alcohols, such as, for example, alkyd resins), polyamides (for example hexamethylenediamine adipate), maleate resins, melamine resins, their precondensates and analogues, polycarbonates and silicones, and d. Polyaddition products, such as polyurethanes (crosslinked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, that is to say, for example, predominantly three-dimensional bodies, such as slabs, profiles, injection mouldings, various machined articles, chips, granules or foams, and also as predominantly two-dimensional bodies, such as films, sheets, lacquers, coverings, impregnations and coatings, or as predominantly one-dimensional bodies, such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints.

b. Mixed with so-called "carriers," wetting agents, plasticisers, swelling agents, anti-oxidants, light stabilisers, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear," "permanent-press" or "no-iron"), as well as flameproof finishes, soft handle finishes, anti-soiling finishes or anti-static finishes, or anti-microbial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches."

f. As additives to the most diverse industrial products in order to render these more marketable (for example improving the appearance of soaps, detergents and pigments).

g. In combination with other optically brightening substances.

h. In spinning bath preparations, that is to say as additives to spinning baths such as are used for improving the slip for the further processing of synthetic fibres, or from a special bath before stretching the fibre.

i. As scintillators for various purposes of a photographic nature, such as, for example, for electrophotographic reproduction or supersensitisation, and for the optical brightening of photographic layers, optionally in combination with white pigments such as, for example, $TiO_2$.

j. Depending on substitution, as laser dyestuffs.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can represent, for example, a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention, is to impregnate these fibres with the aqueous dispersions (or optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so called "slurry" before spraydrying to the washing powder, or during the preparation of liquid washing agent combinations. They can be added either in the form of a solution or dispersion in water or other solvents or, without auxiliaries, as a dry brightening powder. For example, the brighteners can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors," also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The washing agents can further contain, for example: antistatic agents, skin protection agents which restore fat, such as lanolin, enzymes, anti-microbial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibers with a high quality finish, polyester fibres, wool and the like.

The washing treatment is carried out, for example, as follows:

The textiles quoted are treated for 1 to 30 minutes at 20° to 100° C in a wash liquor which contains 1 to 10 g/kg of a composite washing agent containing a builder and 0.05 to 1%, relative to the weight of washing agent, of the brighteners claimed. The liquor ratio can be 1:3 to 1:50. After washing, rinsing and drying are carried out as usual. The wash liquor can contain 0.2 g/l of active chlorine (for example as hypochlorite) or 0.1 to 2 g/l of sodium perborate, as a bleaching additive.

The new optical brighteners are also suitable, depending on substitution, as laser dyestuffs for emission in the region of shortwave visible light.

In the examples, unless otherwise indicated, parts are always parts by weight and percentages are always percentages by weight. Unless otherwise noted, melting points and boiling points are uncorrected.

EXAMPLE 1

4.00 g (0.03 mol) of 2-methyl-benzoxazole of the formula

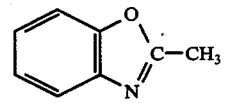

7.50 g (0.03 mol) of 2-phenyl-4-(p-formylphenyl)-2H-1,2,3-triazole of the formula

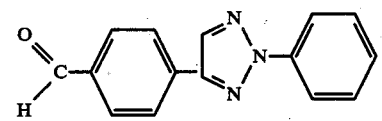

(melting point: 149° C), 6.55 g (0.035 mol) of toluene-4-sulphonic acid monohydrate and 2.85 g (0.039 mol) of dimethylformamide are stirred in 60 ml of xylene for 90 minutes under reflux, in a sulphonating flask which is provided with a water separator, during which 1.17 ml of water are isolated by xylene/water azeotropic distillation. The reaction mixture is then cooled to room temperature and the product is filtered off and washed with 50 ml of toluene. The olive-green product is suspended in water, the aqueous suspension is adjusted to pH 10 with 2 N sodium hydroxide solution, warmed to 40° C and filtered whilst warm. This gives 10.1 g (corresponding to 92% of theory) of the compound 2-[-4-(2'-phenyl-(2H)-1,2,3-triazolyl(4')-styryl)-]-benzoxazole of the formula

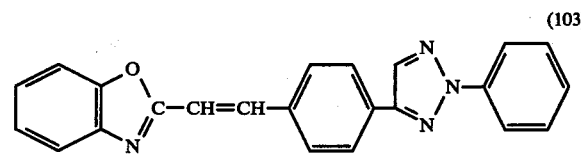

as a green-yellow product. After recrystallising twice from chlorobenzene (fuller's earth) 6.4 g of greenish-tinged yellow crystals of melting point 217°–218° C are obtained.

Analysis: $C_{23}H_{16}N_4O$ (364.39)
calculated: C, 75.81; H, 4.43; N, 15.38.
found: C, 75.80; H, 4.20; N, 15.40.

The compounds of the formula

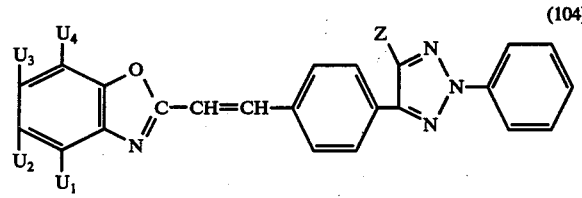

listed in the table which follows can be manufactured in an analogous manner.

TABLE I

| No. | $U_1$ | $U_2$ | $U_3$ | $U_4$ | Z | Melting point° C |
|---|---|---|---|---|---|---|
| 105 | H | H |  | H | H | 215 – 216 |
| 106 | H | —$SO_2CH_3$ | H | H | H | 264 |
| 107 | H | —$CH_3$ | H | H | H | 214 |
| 108 | H | —$CH_2CH_2CN$ | H | H | H | 208 |

TABLE I-continued

| No. | U₁ | U₂ | U₃ | U₄ | Z | Melting point° C |
|-----|----|----|----|----|---|------------------|
| 109 |  | | H | H | H | 198 |
| 110 | H |  | H | H | H | 219 |
| 111 | H | —CH₃ | —CH₃ | H | H | 224 |
| 112 | H | —CH₃ | H | —CH₃ | H | 200 |
| 113 | H | —OCH₃ | H | H | H | 205 |
| 114 | H | —C(CH₃)₃ | H | H | H | 172 |
| 115 | H | Cl | H | H | H | 223 |
| 116 | H | —C(CH₃)₂ | H | H | H | 180 |
| 117 | H |  | H | H | H | 253 |
| 118 | H | —COOCH₃ | H | H | H | 229 |
| 119 | H | NaSO₃— | H | H | H | recrystallised from water/ethanol |
| 120 | H | —CH₂CH₂CN | H | H | Cl | 184 |
| 121 | H | H | H | H | Cl | 186 |
| 122 | H | H | H | H |  | 187 |

EXAMPLE 2

4.39 g (0.021 mol) of 5-phenyl-2-methyl-benzoxazole of the formula

(201)

4.54 g (0.02 mol) of 2-(p-methylsulphonyl-phenyl)-4-(p-formylphenyl)-(2H)-1,2,3-triazole of the formula

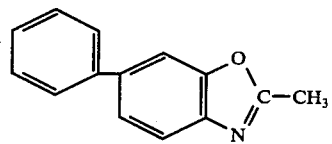

(202)

(melting point: 330° C), 4.37 g (0.023 mol) of toluene-4-sulphonic acid monohydrate and 1.90 g (0.026 mol) of dimethylformamide are stirred in 50 ml of xylene for 1 hour under reflux, in a sulphonating flask which is provided with a water separator. The white suspension is converted to a brown solution, 2.00 ml of water being isolated by xylene/water azeotropic distillation. The reaction mixture is then cooled to room temperature and the product is filtered off and washed with 60 ml of toluene. The brown product is suspended in water, the aqueous suspension is adjusted to pH 10 with 2 N sodium hydroxide solution, warmed to 40° C and filtered whilst warm. This gives 5.7 g (corresponding to 79.3% of theory) of the compound 2-[-4-(2'-p-methylsulphonylphenyl)-(2'H)-1',2',3'-triazolyl(4')-styryl-]-benzoxazole of the formula

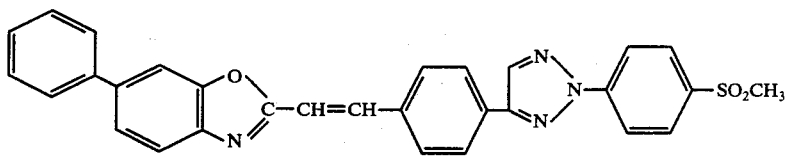

(203)

as a pale yellow product. After recrystallising twice from dimethylformamide (active charcoal) 2.7 g of greenishtinged yellow crystals of melting point above 300° C are obtained.

Analysis: C₃₀H₂₂N₄O₃S (518.60)
calculated: C, 69.48; H, 4.28; N, 10.80.
found: C, 69.40; H, 4.40; N, 10.90.

2-Phenyl-4-(p-formylphenyl)-2H-1,2,3-triazole of the formula

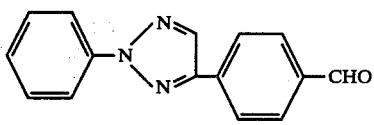

(204)

used as the starting material for the manufacture of the compound of the formula (103) can be prepared as follows:

5.7 g (0.065 mol) of 2-nitropropane are introduced into a solution of 1.15 g (0.05 mol) of sodium in 1,000 ml of ethanol at about 20° C. The reaction mixture is stirred for 1 hour and warmed to 35° C, and 16.0 g (0.05 mol) of 2-phenyl-4-(p-bromomethylphenyl)-2H-1,2,3-triazole are now added. The solution is then stirred for 20 hours, without external warming, and the suspension formed is filtered off and washed with water until neutral. A further amount of product can be obtained by concentrating the mother liquor. After recrystallisation from ethanol, 8.9 g (corresponding to 69.5% of theory) of the compound of the formula (204) are obtained as a white crystalline powder of melting point 149° C.

The two aldehydes of the formulae

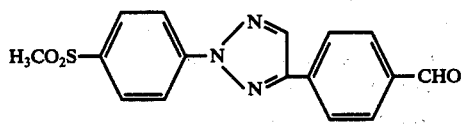

melting point: 210° C and

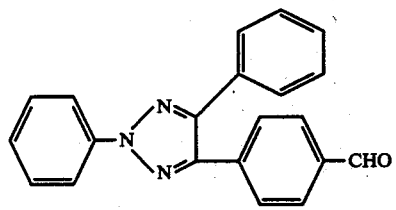

melting point: 140° C, can be manufactured according to the same process.

2-Phenyl-4-(p-formylphenyl)-5-chloro-v-triazole of the formula

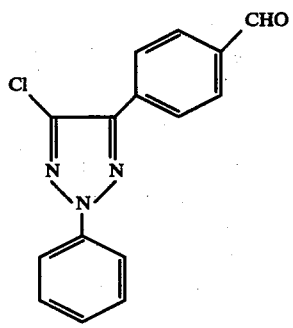

is manufactured as follows:

1-N-Oxy-2-phenyl-4-tolyl-v-triazole is dissolved in a dioxane/water solvent mixture, hydrogen chloride is passed in at 90° C for 9 hours and the reaction mixture is then evaporated and the residue is recrystallised from hexane. The product, that is to say 2-phenyl-4-tolyl-5-chloro-v-triazole, (melting point 87°–88° C) is reacted with bromosuccinimide, in carbon tetrachloride as the solvent and using a catalytic amount of dibenzoyl peroxide, to give 2-phenyl-4-(p-bromomethylphenyl)-5-chloro-v-triazole (melting point 121°–122° C). From this compound, the compound 2-phenyl-4-(p-formylphenyl)-5-chloro-v-triazole of melting point 119° C is manufactured according to the same process as that described for the compound (204).

2-Methyl-benzoxazole-5-propionitrile (starting material for the compounds (108) and (120)) of the formula

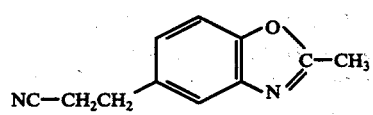

is manufactured as follows:

4-Hydroxy-phenyl-propionitrile is nitrated in glacial acetic acid with 65% strength nitric acid at 10°–15° C, in the course of 2 hours, the 3-nitro-4-hydroxyphenyl-propionitrile (melting point = 104° C) is reduced with hydrogen, using 5% strength palladium charcoal as the catalyst, in ethanol at room temperature to give 3-amino-4-hydroxyphenyl-propionitrile (melting point = 125° C) and the amine compound is acetylated in toluene with molar equivalent amounts of acetic anhydride. The 3-acetamino-4-hydroxyphenyl-propionitrile (melting point = 191°–192°) is slowly warmed to 250°–260° and then rapidly heated up to 300°. The melt is cooled to room temperature, the oil is taken up in an alkaline aqueous solution, the pH of which is adjusted to 10, and the water/oil emulsion is extracted by shaking with chloroform. The chloroform solution is separated from the aqueous phase, dried with sodium sulphate and concentrated. The pink-beige needle crystals thus obtained melt at 69°–70° C.

EXAMPLE 3

A polyester fabric (25 g) is placed in a bath, which contains, per liter, 10 g of a condensation product of aromatic sulphonic acids, 25 g of an aromatic carboxylic acid ester, as the emulsifier, and 5 g of sodium dihydrophosphate and which is adjusted to a pH value of 5 with acetic acid, in a liquor ratio of 1:40. After a dyeing time of one hour at the boiling point in the presence of 0.05 g/l of a brightener of the formula (103) or (107), the fabric exhibits a brilliant brightening with good fastness to light.

EXAMPLE 4

0.01 percent by weight of a brightener of the formula (103), (105), (106), (107), (112) or (203) is milled into opaque soft polyvinyl chloride. The polyvinyl chloride exhibits a neutrally white brightening with good fastness to light.

EXAMPLE 5

100 Parts of polyester granules consisting of terephthalic acid ethylene glycol polyester are intimately mixed with 0.05 part of a compound of the formula (107) or (108) and the mixture is fused at 285° C, whilst stirring. After extruding the spinning composition through customary spinnerets, strongly brightened polyester fibres of good fastness to light are obtained.

The abovementioned compounds can also be added to the starting materials before or during the polycondensation to give the polyester.

EXAMPLE 6

A polyester fabric (for example "DACRON") is padded at room temperature (about 20° C) with an aqueous dispersion which contains, per liter, 2 g of one of the compounds of the formula (103), (107) or (108) and 1 g of an addition product of about 8 mols of ethylene oxide and 1 mol of p-tert.-octylphenol, and is dried at about 100° C. The dry material is then subjected to a heat treatment of 170° to 220° C, which, depending on the temperature, lasts 2 minutes to a few seconds. The material treated in this way exhibits a strong brightening effect of good fastness to light.

EXAMPLE 7

0.06 g of Tinegal NA (= alkyl polyglycol ether) is added to 100 ml of water.

A solution of an optical brightener of the formula (103) is prepared by dissolving 1 g in 1,000 ml of dimethylformamide. 3 ml of this stock solution are added to the solution described above. This aqueous solution or dispersion, which contains the brightener, is warmed to 60° C, and a nylon fabric weighing 3 g is then placed in the solution. The temperature is increased in the course of 10–15 minutes to 92°–95° C and the bath is left at this temperature for 30 minutes. The fabric is then rinsed for 2 minutes in running cold water and is then dried for 20 minutes at 60° C.

The fabric treated in this way exhibits a significant brightening effect of good fastness to light.

Analogous effects are achieved with the optical brighteners of the formulae (107) or (108).

EXAMPLE 8

A fabric of polyamide fibre (Perlon) is placed into a bath, which, (relative to the weight of the material) contains 0.1% of one of the brighteners of the formulae (103), (107) or (108), and, per liter, 1 g of 80% strength acetic acid and 0.25 g of an addition product of 30 to 35 mols of ethylene oxide and one mol of industrial stearyl alcohol, in a liquor ratio of 1:40 at 60° C. The bath is warmed to the boiling point in the course of 30 minutes and is maintained at the boil for 30 minutes. After rinsing and drying the fabric, a strong brightening effect of good fastness to light is obtained.

If a fabric consisting of polyamide-66 (nylon) is used instead of the fabric consisting of polyamide-6, brightening effects which are similarly good are achieved.

Finally, the process can also be carried out under high temperature conditions, for example for 30 minutes at 130° C. For this type of use it is advisable to add 3 g/l of hydrosulphite to the liquor.

EXAMPLE 9

0.4 g of a washing agent of the following composition is added to 100 ml of water:

| | |
|---|---|
| Dodecylbenzenesulphonate | 16% |
| Fatty alcohol sulphonate | 4% |
| Na tripolyphosphate | 35% |
| Tetra-Na pyrophosphate | 7% |
| Mg silicate (MgSiO$_3$) | 2% |
| Na disilicate (Na$_2$(SiO$_3$)$_2$) | 7% |
| Carboxymethylcellulose | 1% |
| Ethylenediaminetetraacetic acid (sodium salt) | 0.5% |
| Sodium sulphate decahydrate | about 25%* |
| Water | 2.5% |

*(The washing agent can also contain 10-20% of Na perborate or another agent which releases oxygen instead of sodium sulphate decahydrate).

A solution of the optical brightener of the formula (103) is prepared by dissolving 1 g in 1,000 ml of dimethylformamide. 2 ml of this stock solution are added to the solution described above. This aqueous solution (or dispersion) containing the brightener is warmed to 60° C. A nylon fabric weighing 3 g is then placed into the solution and is treated at this temperature for 30 minutes. The fabric is then rinsed for 2 minutes in running cold water and then dried for 20 minutes at 60° C.

The fabric treated in this way exhibits a marked brightening effect of good fastness to light.

Analogous effects are achieved, inter alia, with the optical brighteners of the formula (106), (107) and (108)

EXAMPLE 10

7 g of anatase (TiO$_2$) are added to 1,400 ml of dimethylformamide and then 350 g of polyacrylonitrile, in powder form, are added and the mixture is processed by means of highspeed stirrer to give a viscous composition. 5 mg of a brightener of the formula (105), (109) or (112) are added to 50 g of this 20% strength solution. This mixture is homogenised by stirring and then kept under a vacuum for one hour to enable the air bubbles formed to diffuse out. After this, the composition is poured onto a glass plate and drawn out with a metal rod to give a uniform film. The polyacrylonitrile film is then dried in a drying cabinet for about 15 minutes at about 50° C, with ventilation (draught of air), and then dried at room temperature with slight ventilation. The polyacrylonitrile film can be easily separated from the glass plate. It possesses a substantially higher white effect with good fastness to light than a film manufactured identically which does not contain the optical brightener.

We claim:

1. Benzoxazole-styryls of the formula

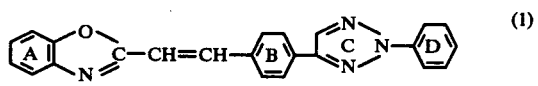

wherein the rings A, B, C and D are unsubstituted or substituted with non-chromophoric substituents, selected from the group consisting of unsubstituted alkyl with 1 to 4 carbon atoms, alkyl with 1 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylakyl with 1 to 3 carbon atoms in the alkyl part, phenyl which is optionally substituted by 1 or 2 substituents from the series chlorine, methyl or methoxy; alkoxy with 1 to 4 carbon atoms, phenoxy which is optionally substituted by 1 or 2 substituents from the series chlorine, methyl or methoxy; chlorine, bromine, cyano, COOR, wherein R represents hydrogen, a salt-forming cation, alkyl with 1 to 5 carbon atoms or benzyl, CONR' (R$_1$'), wherein R' represents hydrogen, alkyl with 1 or 6 carbon atoms, alkyl with 2 to 4 carbon atoms, which is substituted at the terminal carbon atom by a dialkylamino group or an optionally quaternised dialkylamino group with 1 to 4 carbon atoms in each alkyl part, hydroxyalkyl with 1 to 4 carbon atoms, alkoxyalkyl with 2 to 8 carbon atoms, phenyl or benzyl and R$_1$' represents hydrogen, alkyl with 1 to 6 carbon atoms, hydroxyalkyl with 1 to 4 carbon atoms or alkoxyalkyl with 2 to 8 carbon atoms, or R' and R$_1$', conjointly with the nitrogen, represent a morpholino or piperidino radical; SO$_2$OY, wherein Y denotes hydrogen, a salt-forming cation, alkyl with 1 to 5 carbon atoms, phenyl or alkyl-substituted phenyl SO$_2$NR' (R$_1$'), wherein R' and R$_1$' have the meaning indicated above, alkylsulphonyl with 1 to 6 carbon atoms, benzylsulphonyl, phenylsulphonyl or phenylsulphonyl which is substituted by chlorine or methyl, or a fused phenyl ring.

2. Benzoxazole-styryls according to claim 1, of the formula

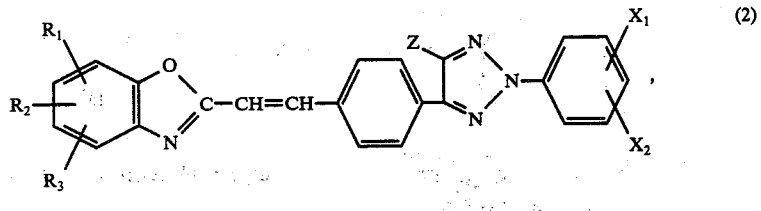

wherein $R_1$ denotes hydrogen, unsubstituted alkyl with 1 to 4 carbon atoms, alkyl with 1 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylalkyl with 1 to 3 carbon atoms in the alkyl part, phenyl which is optionally substituted by 1 or 2 substituents from the series chlorine, methyl or methoxy; alkoxy with 1 to 4 carbon atoms, phenoxy which is optionally substituted by 1 or 2 substituents from the series chlorine, methyl or methoxy; chlorine, bromine, cyano, COOR, wherein R represents hydrogen, a salt-forming cation, alkyl with 1 to 5 carbon atoms or benzyl, CONR' ($R_1'$), wherein R' represents hydrogen, alkyl with 1 to 6 carbon atoms, alkyl with 2 to 4 carbon atoms, which is substituted at the terminal carbon atom by a dialkylamino group or an optionally quaternised dialkylamino group with 1 to 4 carbon atoms in each alkyl part, hydroxyalkyl with 1 to 4 carbon atoms, alkoxyalkyl with 2 to 8 carbon atoms, phenyl or benzyl and $R_1'$ represents hydrogen, alkyl with 1 to 6 carbon atoms, hydroxyalkyl with 1 to 4 carbon atoms or alkoxyalkyl with 2 to 8 carbon atoms, or R' and $R_1'$, conjointly with the nitrogen, represent a morpholino or piperidino radical; $SO_2OY$, wherein Y denotes hydrogen, a salt-forming cation, alkyl with 1 to 5 carbon atoms, phenyl or alkyl-substituted phenyl, $SO_2NR'$ ($R_1'$), wherein R' and $R_1'$ have the meaning indicated above, alkylsulphonyl with 1 to 6 carbon atoms, benzylsulphonyl, phenylsulphonyl or phenylsulphonyl which is substituted by chlorine or methyl, or $R_1$, conjointly with $R_2$, denotes a fused phenyl ring, $R_2$ denotes hydrogen, alkyl with 1 to 5 carbon atoms, alkoxy with 1 to 4 carbon atoms or chlorine or, conjointly with $R_1$, a fused phenyl ring, $R_3$ denotes hydrogen or methyl, $X_1$ denotes hydrogen, alkyl with 1 to 4 carbon atoms, cyclohexyl, phenylalkyl with 1 to 3 carbon atoms in the alkyl part, phenyl, alkoxy with 1 to 4 carbon atoms, phenoxy, chlorine, cyano, COOR, CONR' ($R_1'$), $SO_2OY$, $SO_2NR'$ ($R_1'$), wherein Y, R, R' and $R_1'$ each have the abovementioned meaning, alkylsulphonyl with 1 to 6 carbon atoms, benzylsulphonyl, phenylsulphonyl or phenylsulphonyl which is optionally substituted by chlorine or methyl, $X_2$ denotes hydrogen, chlorine, methyl or methoxy and Z denotes hydrogen, chlorine or phenyl.

3. Benzoxazole-styryls according to claim 1, of the formula

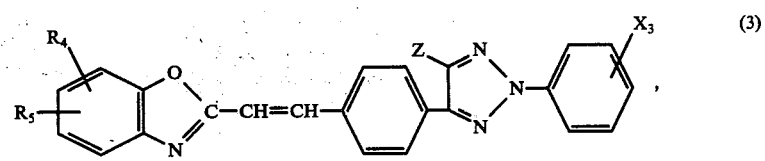

wherein $R_4$ denotes hydrogen, chlorine, unsubstituted alkyl with 1 to 4 carbon atoms, alkyl, with 2 to 3 carbon atoms, which is substituted at the terminal carbon atom by a cyano group or COOR group, wherein R represents hydrogen, a salt-forming cation or alkyl with 1 to 5 carbon atoms, cyclohexyl, phenylalkyl with 1 to 3 carbon atoms in the alkyl part, phenyl or alkoxy with 1 to 4 carbon atoms, $R_5$ denotes hydrogen or alkyl with 1 to 4 carbon atoms, $X_3$ denotes hydrogen, alkyl with 1 to 4 carbon atoms, alkoxy with 1 to 4 carbon atoms, chlorine, carbalkoxy with 2 to 5 carbon atoms, sulphamoyl or sulphamoyl which is monosubstituted or disubstituted by alkyl with 1 to 4 carbon atoms or hydroxyalkyl with 2 to 4 carbon atoms, or alkylsulphonyl with 1 to 4 carbon atoms and Z denotes hydrogen, chlorine or phenyl.

4. Benzoxazole-styryls according to claim 1, of the formula

![Formula 4]

wherein $R_4'$ denotes hydrogen, chlorine, unsubstituted alkyl with 1 to 4 carbon atoms, alkyl, with 2 to 3 carbon atoms, which is substituted at the terminal carbon atom by a cyano group or COOR group, wherein R represents hydrogen, sodium, potassium or alkyl with 1 to 5 carbon atoms, cyclohexyl, phenyl, alkoxy with 1 to 4 carbon atoms or alkylsulphonyl with 1 to 4 carbon atoms, $R_5$ denotes hydrogen or alkyl with 1 to 4 carbon atoms and Z denotes hydrogen, chlorine or phenyl.

5. Benzoxazole-styryls according to claim 1, of the formula

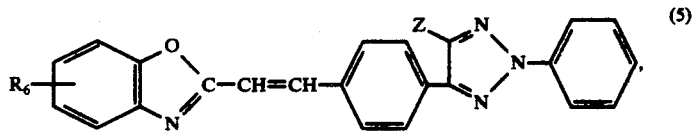

wherein $R_6$ denotes hydrogen, chlorine, alkyl with 1 to 4 carbon atoms, β-cyanoethyl, cyclohexyl, phenyl or alkoxy with 1 to 4 carbon atoms and Z denotes hydrogen, chlorine or phenyl.

6. Benzoxazole-styryls according to claim 1, of the formula

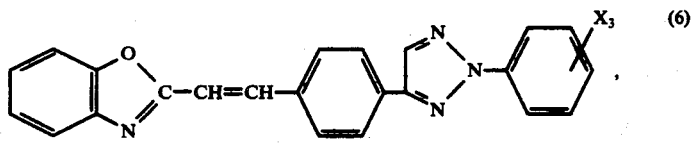

wherein $X_3$ denotes hydrogen, alkyl with 1 to 4 carbon atoms, alkoxy with 1 to 4 carbon atoms, chlorine, carbalkoxy with 2 to 5 carbon atoms, sulphamoyl which is optionally monosubstituted or disubstituted by alkyl with 1 to 4 carbon atoms or hydroxyalkyl with 2 to 4 carbon atoms, or alkylsulphonyl with 1 to 4 carbon atoms.

7. Benzoxazole-styryl according to claim 1, of the formula (6a)

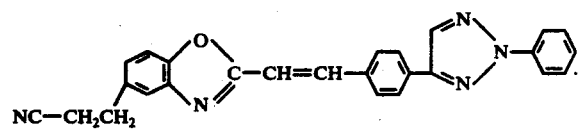

* * * * *